(12) United States Patent
Kinoshita et al.

(10) Patent No.: US 6,656,438 B1
(45) Date of Patent: Dec. 2, 2003

(54) DISINFECTANT SOLUTION BOTTLE

(75) Inventors: Toshiharu Kinoshita, Hino (JP); Mikihiko Nakagawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/497,725

(22) Filed: Feb. 4, 2000

(30) Foreign Application Priority Data

Feb. 5, 1999 (JP) .......................................... 11-028863

(51) Int. Cl.[7] ................................................ A61L 2/00
(52) U.S. Cl. ..................... 422/292; 422/300; 422/28; 215/390; 215/400; 215/386
(58) Field of Search ................. 422/292, 300, 422/28; 215/390, 386, 391, 400, 247, 47

(56) References Cited

U.S. PATENT DOCUMENTS

| | | | | |
|---|---|---|---|---|
| 844,579 A | * | 2/1907 | Clements ..................... 215/382 |
| 4,269,722 A | * | 5/1981 | Joshi et al. ................... 510/293 |
| 5,002,199 A | * | 3/1991 | Frahm ......................... 220/670 |
| 5,279,799 A | * | 1/1994 | Moser .......................... 422/292 |
| D373,537 S | * | 9/1996 | Schirado ....................... D9/572 |
| D380,148 S | * | 6/1997 | Hauf et al. .................... D9/337 |
| 5,863,421 A | * | 1/1999 | Peter et al. ................... 210/134 |
| 5,915,578 A | * | 6/1999 | Burt ............................ 215/250 |
| D439,156 S | * | 3/2001 | Hall et al. .................... D9/341 |

FOREIGN PATENT DOCUMENTS

| | | | |
|---|---|---|---|
| EP | 0 232 170 B1 | 2/1987 | ............. A61L/2/24 |
| EP | 0 507 461 B1 | 3/1992 | ............. A61L/2/18 |

\* cited by examiner

Primary Examiner—Robert J. Warden, Sr.
Assistant Examiner—Sean E. Conley
(74) Attorney, Agent, or Firm—Kenyon & Kenyon

(57) ABSTRACT

Since the disinfectant solution bottle has a detachable section and a sealing section, the disinfectant solution bottle can be connected to the inlet of the disinfectant solution tank of the cleaning and disinfecting unit in a watertight manner; the mouth section of the bottle is closed with the sealing section before the disinfectant solution bottle is attached to the inlet of the disinfectant solution tank; and while the disinfectant solution is being connected to the inlet of the disinfectant solution tank, the disinfectant solution or concentrated disinfectant solution in the disinfectant solution bottle can flow into the disinfectant solution tank via the inlet because the inside of the disinfectant solution bottle and the inside of the disinfectant solution tank can communicate with each other in a watertight manner cut off from the outside, for example, due to automatic rupture of the sealing section when the disinfectant bottle is attached to the inlet of the disinfectant solution tank.

24 Claims, 9 Drawing Sheets

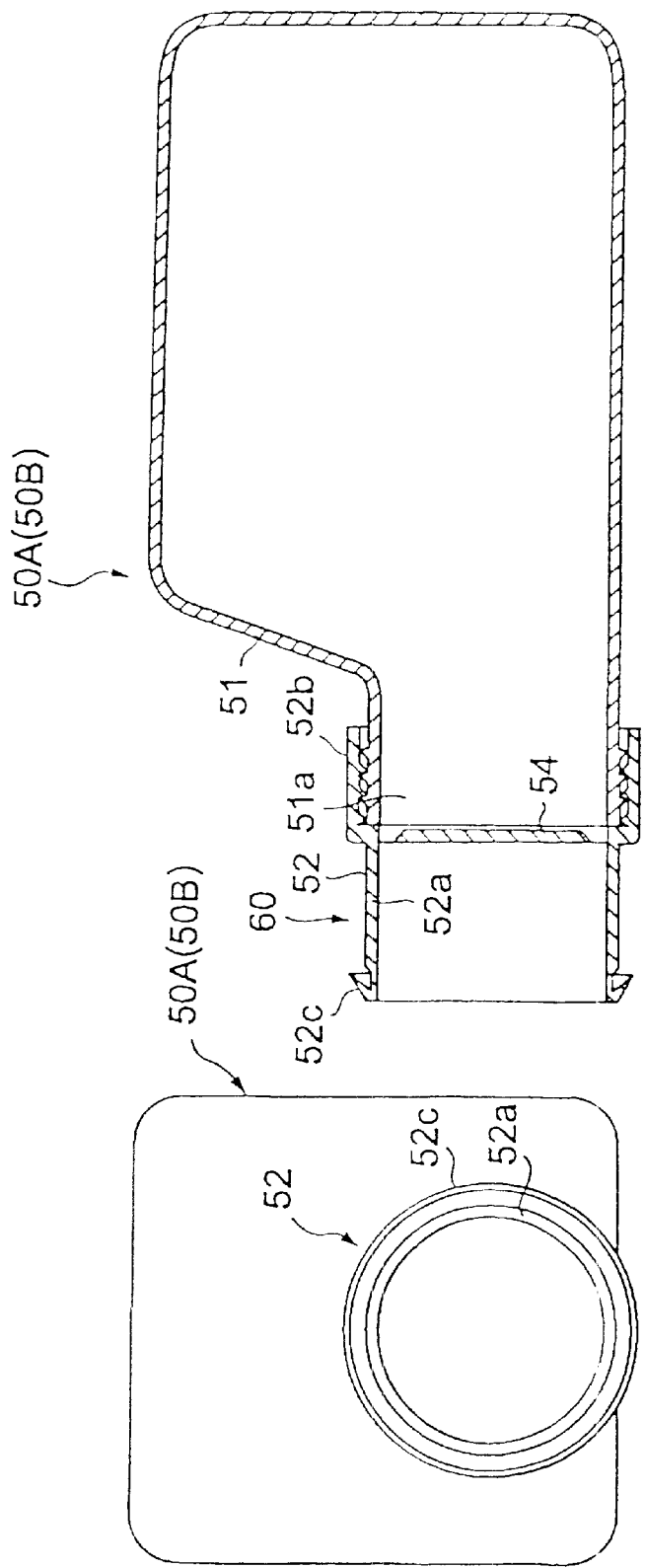

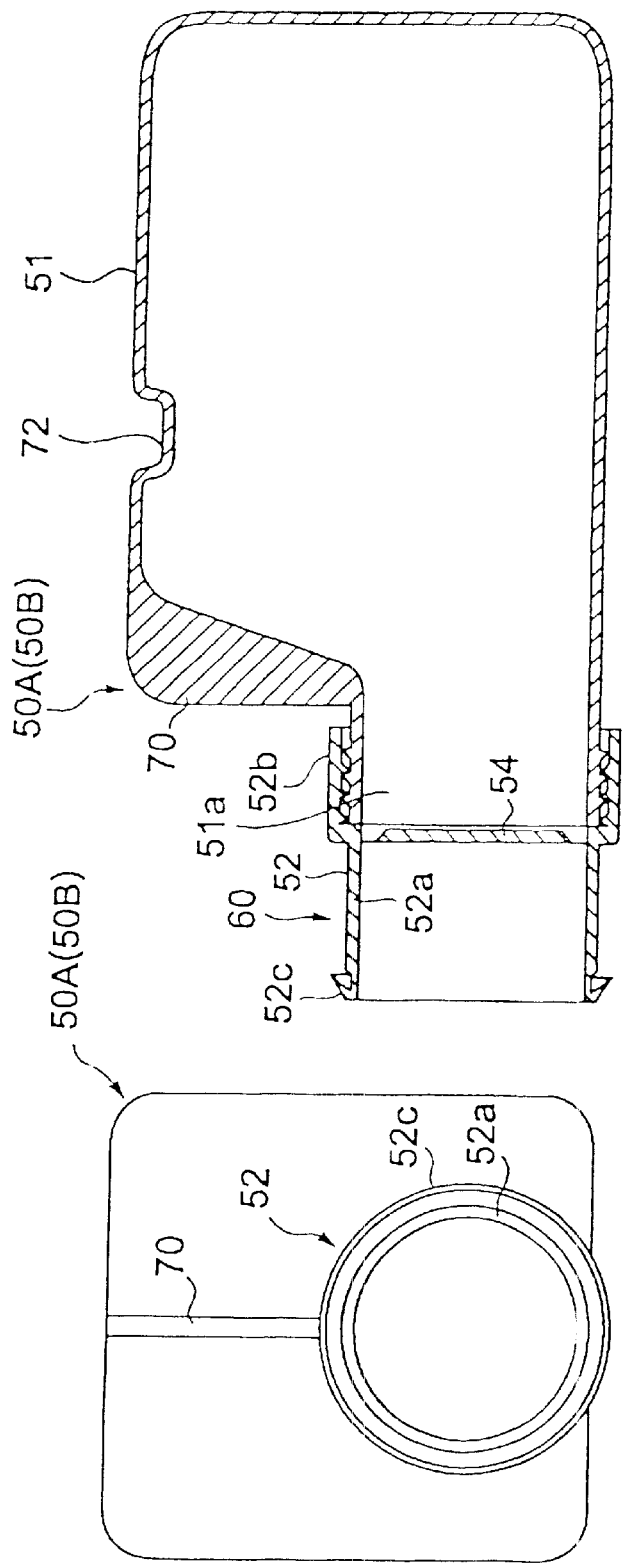

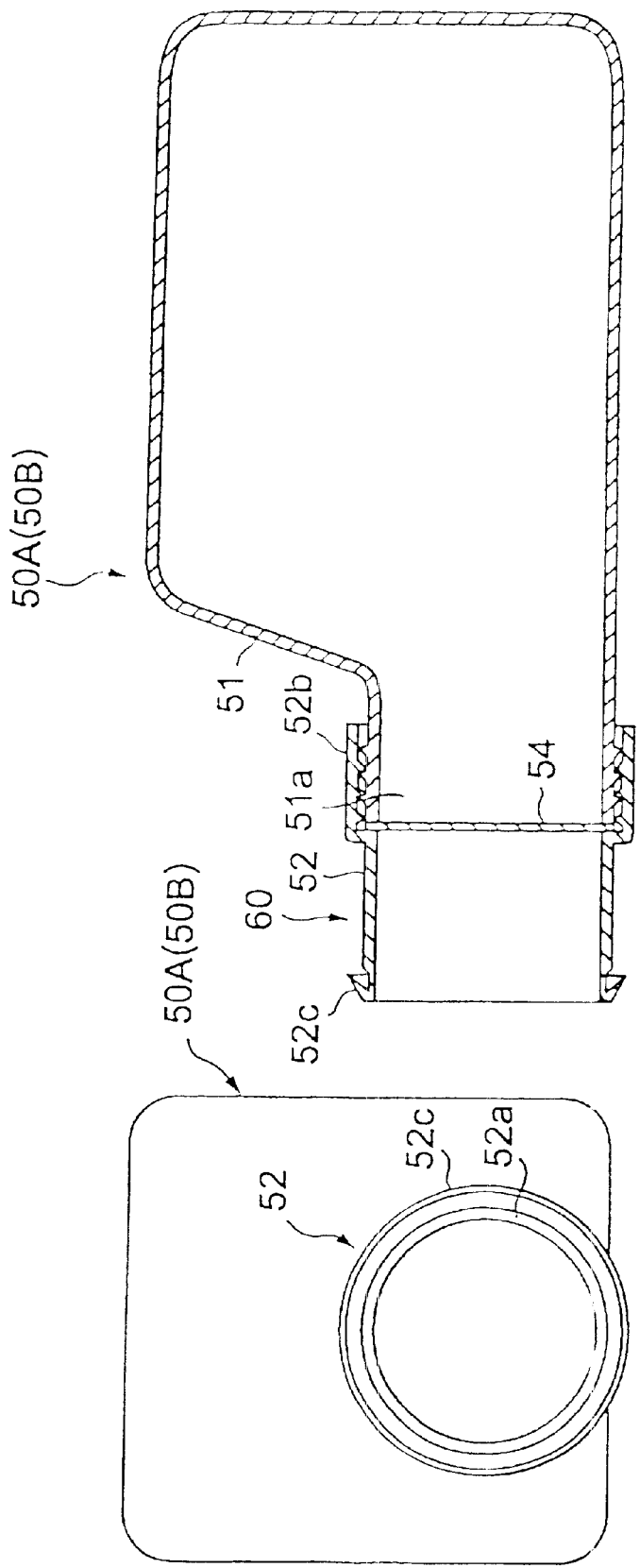

DISINFECTANT SOLUTION BOTTLE

BACKGROUND OF THE INVENTION

1. Field of the Invention

The present invention relates to a disinfectant solution bottle for holding a disinfectant solution or concentrated disinfectant solution, particularly a disinfectant solution bottle detachably attached to a disinfectant tank of an endoscope cleaning and disinfecting unit for cleaning and disinfecting an endoscope.

2. Description of the Related Art

Traditionally, endoscopes have been widely used for examination or treatment of a body cavity. An endoscope includes a variety of ducts for air supply, water supply, aspiration, etc. Its external surface and internal ducts must be cleaned and disinfected after each use.

Traditionally, various types of endoscope cleaning and disinfecting units have been used to clean and disinfect endoscopes. In principle, however, an endoscope is cleaned and disinfected in a cleaning tank through a series of processes constituted of cleaning the endoscope with cleaning water, disinfecting the cleaned endoscope with a disinfectant solution, rinsing, and drying.

During the above-mentioned disinfecting process, a pre-determined disinfectant solution is supplied to the cleaning tank from a disinfectant solution tank arranged within the unit. A pre-determined quantity of disinfectant and sterilizing solution (hereinafter referred to as "disinfectant solution" simply) is stored in the disinfectant solution tank in advance. The disinfectant solution stored in the disinfectant solution tank is produced by diluting a concentrated disinfectant solution with diluting water. Traditionally, a disinfectant solution is prepared in a specific preparation place such as a sink by the user. Then the prepared disinfectant solution is injected into the disinfectant solution tank from the inlet of the disinfectant solution tank by the user.

In the traditional case in which a disinfectant solution is prepared in a specific preparation place by the user, it is not easy to obtain a predetermined concentration of disinfectant solution.

BRIEF SUMMARY OF THE INVENTION

The present invention has been made in consideration of the above-mentioned problem.

An aspect of the present invention is a disinfectant solution bottle detachably attached to the inlet of the disinfectant solution tank of a cleaning and disinfecting unit including a cleaning tank and a disinfectant solution tank for holding a disinfectant solution to be supplied to said cleaning tank. The disinfectant solution bottle comprises a bottle body for holding a disinfectant solution or concentrated disinfectant solution, a detachable section disposed at the mouth section of said bottle body and detachably attached to the inlet of a disinfectant solution tank, means for closing off said mouth section of said bottle body, the means for closing off ruptured as if said mouth section is opened, and a sealing section disposed on said detachable section, and connected to said inlet of said disinfectant solution tank in a watertight manner for maintaining of the mouth section of said bottle body in a watertight and airtight state relative to the outside.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4(a) is a front view of the mouth section of the bottle shown in FIG. 3.

FIG. 4(b) is a longitudinal-sectional view of the bottle shown in FIG. 3.

FIG. 7(a) is a front view of the mouth section of the bottle according to the second embodiment of the invention.

FIG. 7(b) is a cross-sectional view of the bottle shown in FIG. 7(a).

FIG. 8(a) is a front view of the mouth section of the bottle according to the third embodiment of the invention.

FIG. 8(b) is a cross-sectional view of the bottle shown in FIG. 8(a).

DETAILED DESCRIPTION

Referring to drawings, the embodiments of the present invention will be described as below.

Figure 1:
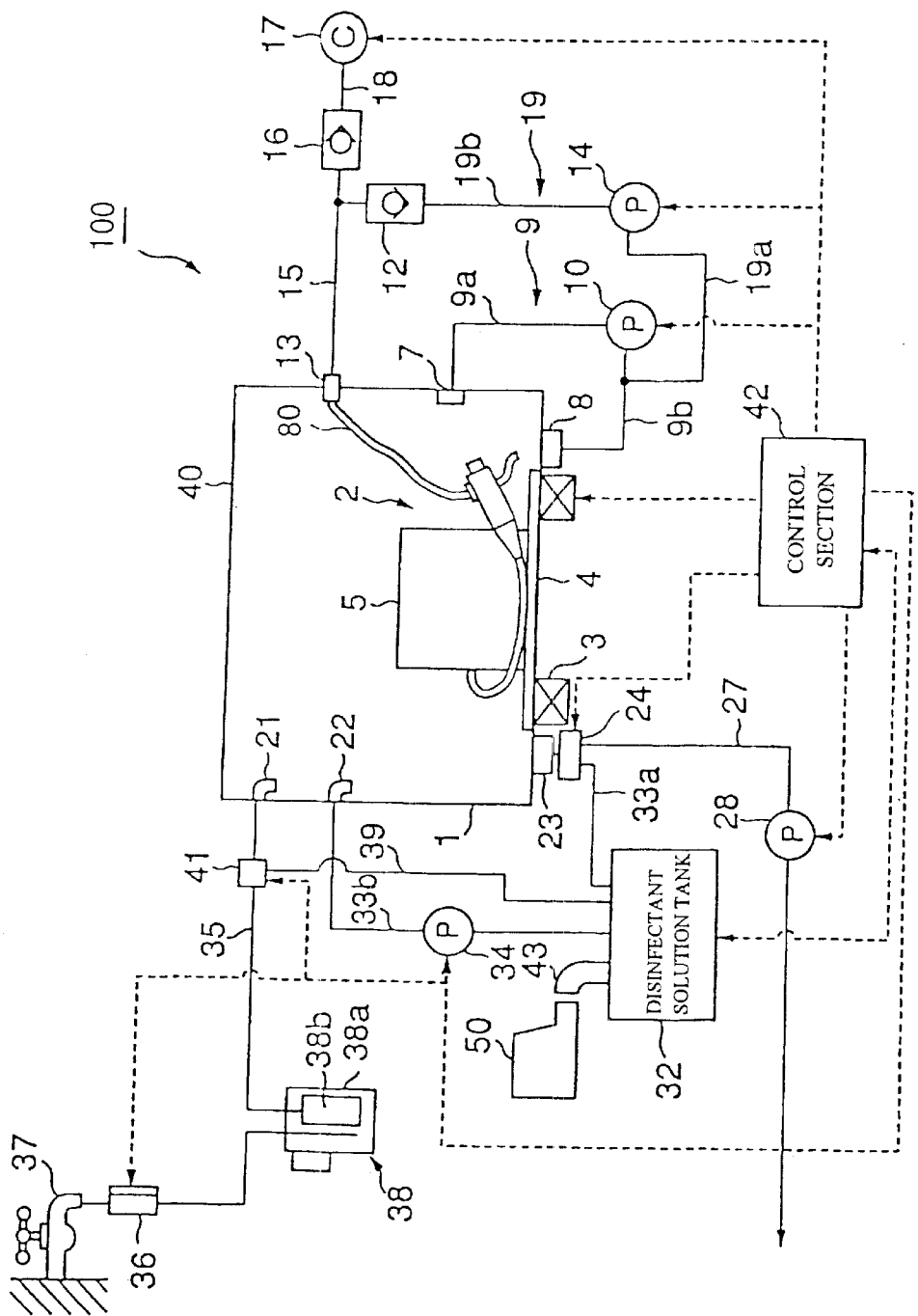
FIG. 1 is a schematic diagram of the endoscope cleaning and disinfecting unit to which the bottle according to the first embodiment of the invention applies.

FIGS. 1 through 6 relate to the first embodiment. FIG. 1 shows the endoscope cleaning and disinfecting unit 100 including a disinfecting solution tank 32 to which the bottle section 50 of the present embodiment holding a concentrated disinfectant solution can be attached. As shown in FIG. 1, the endoscope cleaning and disinfecting unit 100 has a cleaning tank 1 forming its cleaning space: the endoscope 2 can be cleaned and disinfected in the cleaning tank 1. The cleaning tank 1 is provided with a lid 40 forming the top face of the cleaning space that can be opened or closed. Opening the lid 40, the endoscope 2 can be placed in the cleaning tank 1.

A diaphragm 4 is arranged at the bottom of the cleaning tank 1. The diaphragm 4 is, for example, provided with a Langevin-type ultrasonic oscillator 4 to produce oscillations in the cleaning solution stored in the cleaning tank 1.

At the center of the bottom of the cleaning tank 1, is arranged a tower 5 to reduce the quantity of solution in the cleaning tank 1. A heater is arranged in the tower 5 to heat the solution in the cleaning tank 1.

The cleaning tank 1 is provided with a cleaning water inlet 21. To the cleaning water inlet 21, is connected a water duct 35 connected to a faucet 37 of the water source, for example, city water so that cleaning water can be supplied into the cleaning tank 1 through the water duct 35. A water feed valve 36 and a standard water filter for sterilization 38 are arranged on the way in the water duct 35. The water filter 38 is detachably fitted in the filter receiving space within the body of the cleaning and disinfecting unit, comprising a water filter housing 38a and a disposable filter cartridge 38b detachably set in the housing 38a.

A cleaning solution spout 7 is disposed on a sidewall of the cleaning tank 1, and a circulating solution suction mouth 8 is arranged at the bottom of the cleaning tank 1. To the cleaning solution spout 7, is connected a first solution supply duct 9a connected to the discharge side of the first solution supply pump 10, while a second solution duct 9b, connected to the suction side of the first solution supply pump 10, is connected to the circulating solution suction mouth 8. The first and second solution supply ducts 9a and 9b form the first circulatory route 9 through which the solution recovered from the cleaning tank 1 can be pressurized to the cleaning tank 1 again.

On a sidewall of the cleaning tank 1, is arranged a channel connection mouth 13 to which a connection tube 80 is connected. In this case, the connection tube 80 is detachably connected to the connection mouth section that communicates with the internal channel arranged in the operation section of the endoscope 2.

The third solution supply duct 19a branches from the second solution supply duct 9b, and is connected to the suction side of the second solution supply pump 14. To the second solution supply pump 14, is connected the forth solution supply duct 19b. The forth solution supply duct 19b is connected to the fluid supply duct 15 connected to the channel connection mouth 13 via a check valve 12. That is, the third and forth solution supply ducts 19a and 19b form the second circulatory route 19 through which the solution recovered from the cleaning tank 1 can be pressurized to the cleaning tank 1 again through the internal channel of the endoscope 2.

A air supply duct 18 is connected to the midway point of the fluid supply duct 15 via a check valve 16. A compressor 17 is connected to the air supply duct 18 so that compressed air from the compressor 17 can be supplied to the fluid supply duct 15 through the air supply duct 18.

A disinfectant solution inlet 22 is arranged on a sidewall of the cleaning tank 1, and a discharge opening 23 is arranged at the bottom of the cleaning tank 1. To the disinfectant solution inlet 22, is connected a disinfectant solution supply duct 33b connected to the disinfectant solution tank 32 to supply the disinfectant solution from the disinfectant solution tank 32 to the cleaning tank 1 by the suction of the pump 34. A disinfectant solution return duct 33a and a discharge duct 27 are connected to the duct extending from the discharge opening 23 via a duct switching valve 24. The disinfectant solution return duct 33a is connected to the disinfectant solution tank 32 to recover the disinfectant solution from the cleaning tank 1 to the disinfectant solution tank 32. From the disinfectant solution tank 32, extends a diluting solution supply duct 39 that is connected to the midway of the water duct 35 via a duct switching valve 41. That is, in the present embodiment, the duct switching valve 41 and the diluting solution supply duct 39 constitute a diluting solution supply means to supply the cleaning water flowing in the water duct 35 to the disinfectant solution tank 32 as a diluting solution.

A discharge pump 28 is arranged in the discharge duct 27. All of the ultrasonic oscillator 3, pumps 10, 14, 28, and 34, compressor 17, and duct switching valves 24 and 41, and water feed valve 36 are controlled by a control section 42.

Next, the bottle section 50 detachably attached to the disinfectant solution tank 32 and the disinfectant solution tank 32 will be described in more detail.

Figure 2:
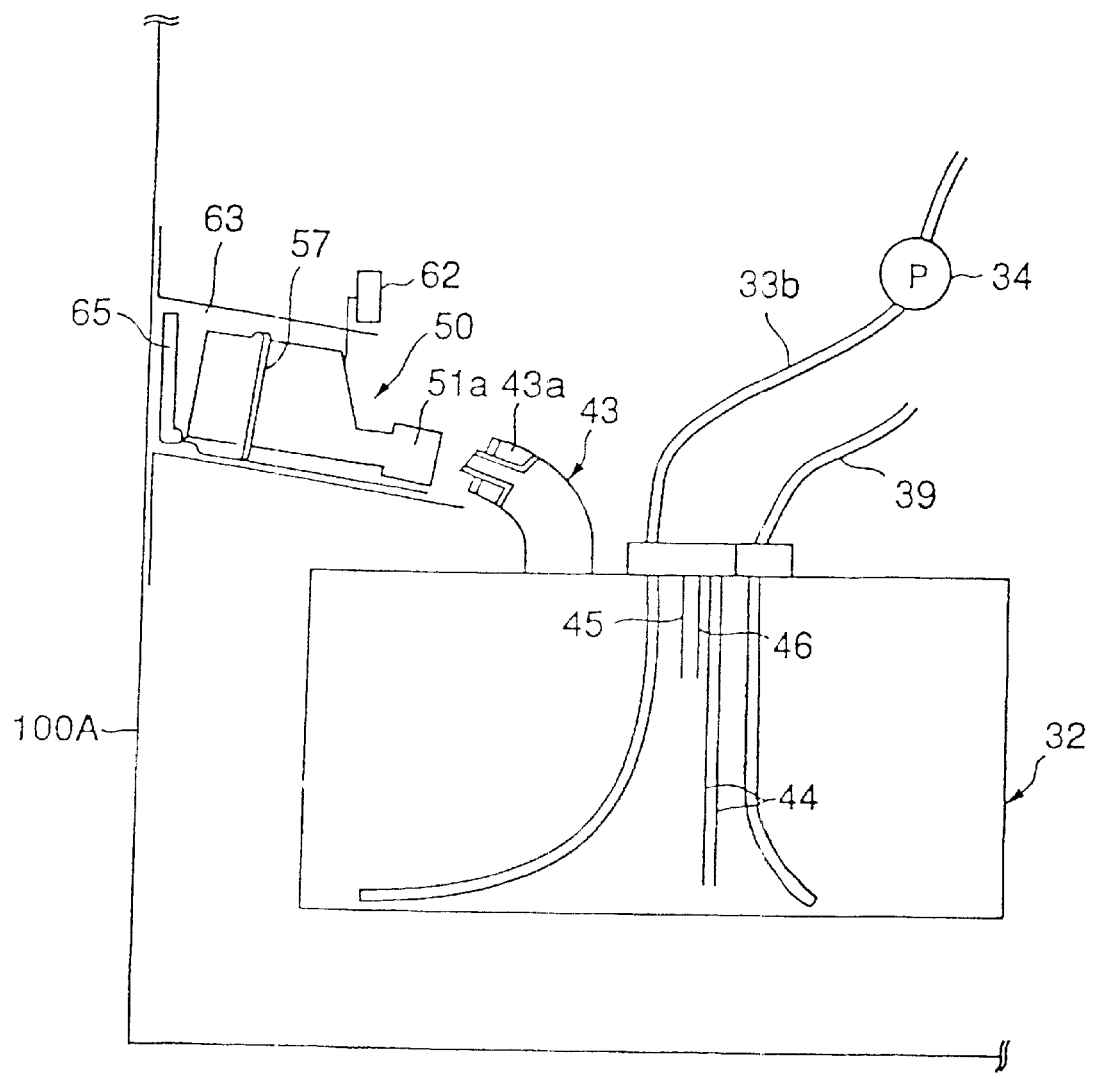
FIG. 2 is a schematic diagram of the disinfectant solution tank, a key part of the endoscope cleaning and disinfecting unit shown in FIG. 1.
Figures 3A, 3B:
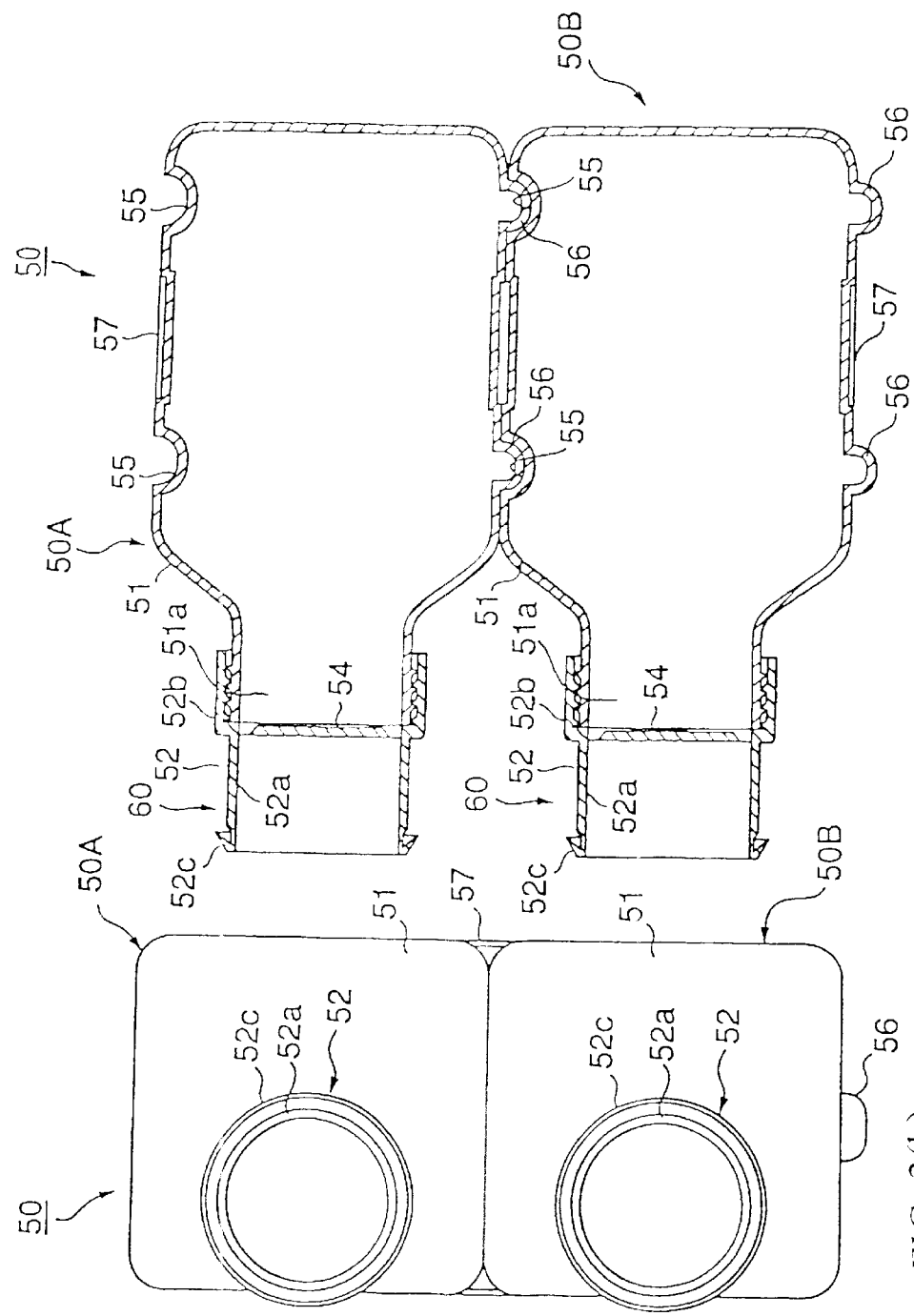
FIG. 3(a) is a cross-sectional view of the bottle to be attached to the disinfectant solution tank shown in FIG. 2.
FIG. 3(b) is a front view of the mouth section of the bottle shown in FIG. 3(a).

As shown in FIG. 2, the disinfectant solution tank 32 is disposed in the body 100A of the cleaning and disinfecting unit 100. On the upper face of the disinfectant solution tank 32, is arranged a mouthpiece-like bottle attaching sections 43 to which the bottle section 50 holding a concentrated disinfectant solution is detachably attached. The bottle attaching section 43 has a curved upper portion so that the opening section is oriented in the lateral direction.

As shown in more detail in FIG. 3, the bottle section 50 attached to the bottle attaching section 43 comprises a first bottle 50A holding a main concentrated solution and a second bottle 50B holding a buffer. Each of the bottles 50A and 50B comprises a bottle-like bottle body 51 in which a solution is stored and a cap 52 which is attached to the mouth section 51a of the bottle body 51. The mouth sections 51a are eccentric to the center axis of the bottle body 51 so that even when the bottles 50A and 50B lie on their side (as shown in FIG. 2), solutions held in the bottles 50A and 50B may be completely discharged through the mouth sections 51a due to their own weight. Specifically, the mouth sections 51a are located on the outer circumference of the bottle body 51 so that the inner face of a sidewall of the bottle body 51 may be on the same plane as the inner face of the mouth sections 51a.

The cap 52, which comprises a cylinder-like cap body 52a, an attachment section 52b formed at the proximal end of the cap body 52a and attached to the bottle body 51, and a sealing section 52c formed at the distal end of the cap body 52a and constituted of an elastic-material member protruding outwardly on the radial direction of the cap 52, constitutes a detachable section 60 detachably attached to the bottle attaching section 43 on the side of the disinfectant solution tank 32. In addition, the cap 52 has a resin film (not renewable once ruptured) that is located at the boundary between the attachment section 52b and the cap body 52a, and can close off the mouth section 51a when the cap 52 is attached to the mouth section 51a of the bottle body 51 via the attachment section 52b.

On a sidewall of the bottle body 51, is arranged a pair of concave sections 55 along the longitudinal axis of the bottle body 51. On another sidewall of the bottle body 51, is arranged a pair of convex sections 56 along the longitudinal axis of the bottle body 51. The first bottle 50A and the second bottle 50B are integrally assembled without longitudinally deviating from each other by engaging the concave sections 55 on a sidewall with the convex sections 56 on another sidewall. In this case, the mouth sections 51a (cap 52) of the bottles 50A and 50B are oriented so that they may be side by side as shown FIG. 3(b). Such an assembled condition is firmly maintained by a shrink film 57 that integrally winds around the sidewalls of the bottles 50A and 50B to thereby form the bottle section 50. Such an assembled condition may be also maintained by welding the bottles 50A and 50B to each other without a shrink film 57.

Figure 5A:
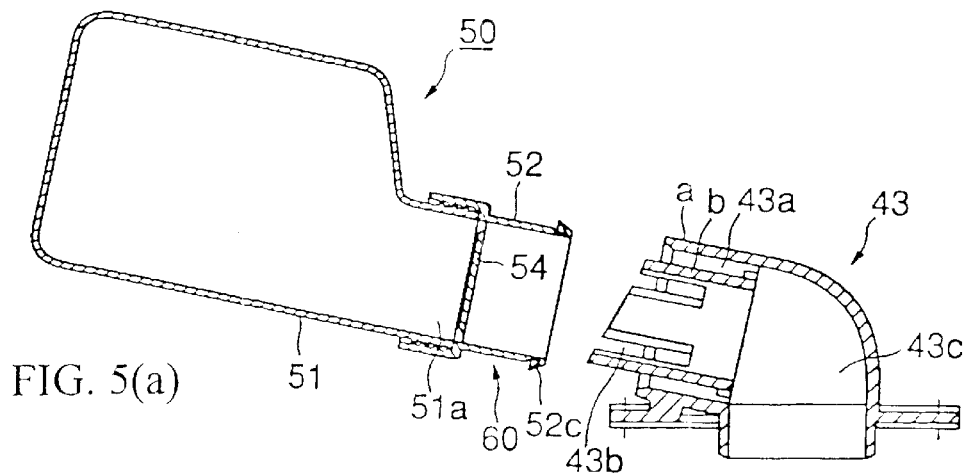
FIG. 5 is a sectional view of the attachment section of the bottle and the disinfectant solution tank.
Figure 5B:
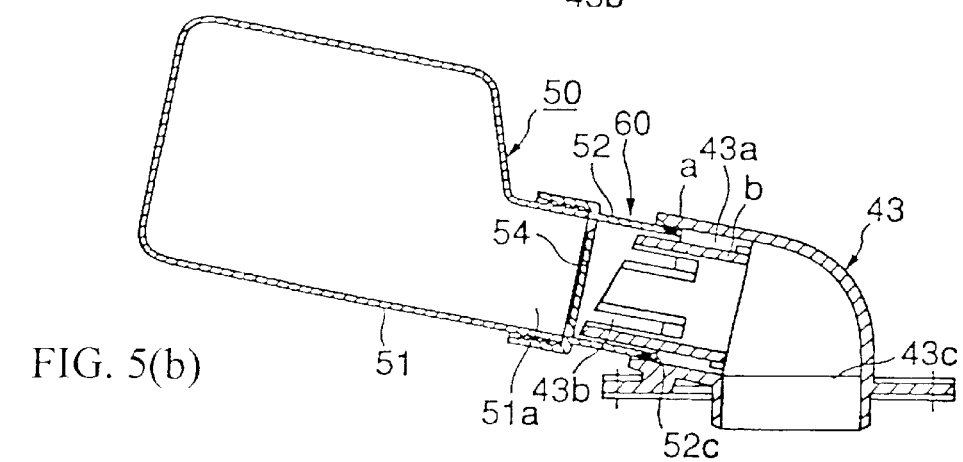
Figure 5C:
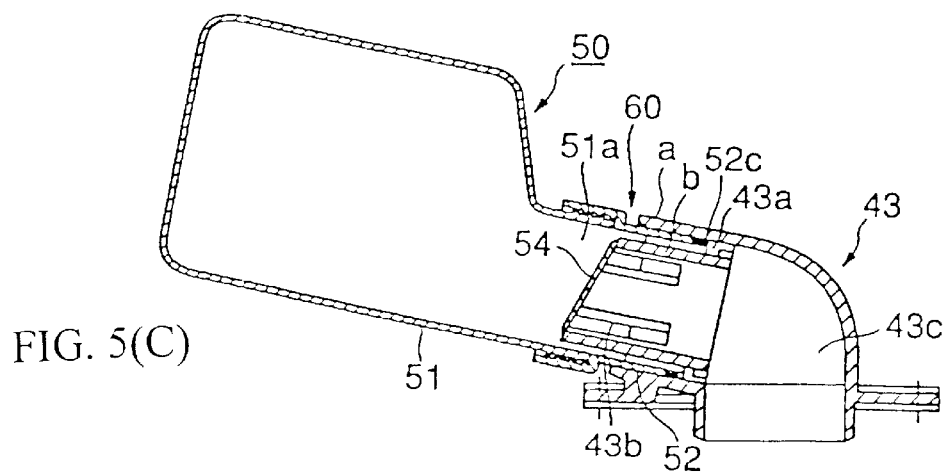

The bottle attaching section 43 detachably attached to the bottle section 50 forms an inlet(channel) from which a concentrated disinfectant solution can be injected into the disinfectant solution tank 32. As shown in detail in FIG. 5, the bottle attaching section 43 has the bottle receiving section 43a for receiving the mouth section 51a of the bottle 50A. Likewise the bottle 50B also includes a mouth receiving section 51a. The bottle attaching section 43 and the mouth section 51a along with the cap 52 form an airtight and watertight seal. An injection port 43c for guiding the concentrated solution into the disinfectant solution tank 32, a pair of protruding sections 43b for allowing the insides of the bottles 50A and 50B to communicate with the inside the disinfectant solution tank 32 by opening the mouth sections 51a of the bottles 50A and 50B while the mouth sections 51a of the bottles 50A and 50B are being received in a watertight manner by the bottle receiving sections as shown in FIG. 5(c).

A bottle receiving section 43a has a two-tube structure comprising an external tube a and an internal tube b arranged in a coaxial manner. In this case, the ring-shaped space between the external tube a and the internal tube b is set for the measurement obtained by fitting the caps 52 of the bottles 50A and 50B, for example, almost the same as the thickness of the cap body 52a. A protruding section 43b is disposed inside the internal tube b, its end face being tapered, and its internal hole communicating with the injection port 43c.

As shown in FIG. 2, a plurality of level sensors 44, 45, and 46 are arranged in the disinfectant solution tank 32 for detecting the quantity of the solution stored in the disinfectant solution tank 32 in stages. The first level sensor 44 can detect the predetermined quantity of a concentrated solution to be injected into the disinfectant solution tank 32 via the concentrated solution bottles 50A and 50B. The second level sensor 45 can detect the quantity of a diluting solution to be supplied for diluting the predetermined quantity of the concentrated solution injected into the disinfectant solution tank 32 (actually, the quantity of the entire disinfectant solution of the predetermined concentration constituted by the diluting solution and the concentrated solution already injected into the tank 32). The third level sensor 46 can detect the minimum quantity required to raise the disinfectant solution to the cleaning tank located in the upper side when starting the unit (the minimum quantity of the disinfectant solution required to appropriately disinfect the endoscope 2 in the cleaning tank 1). Information on detection from the level sensors 44, 45, and 46 is transmitted to the control section 42.

In the present embodiment, the endoscope cleaning and disinfecting unit 100 requires a 15-liter disinfectant solution whose dilution rate is set at 10 times (nine-units of diluting solution to one-unit of concentrated solution). Therefore, the internal volume of the bottle section 50 is set at 1.05 to 2 liters for supplying a concentrated solution. This is because it is necessary to supply at least 1.05-liter concentrated disinfectant solution (concentration rate: 7%) for assuring its effectivity, and at most 2 litters (concentration rate: 13%) for assuring the durability of the endoscope, forceps, or unit to be disinfected.

As shown in FIG. 2, on a sidewall of the unit body 100A, is formed a bottle insertion hole section 63 into which the bottle section 50 is inserted, and which is tilted with an inclination to the obliquely downward direction (in the present embodiment, the tilt angle: 10 degrees). Since the bottle section 50 can be attached to the disinfectant solution tank 32 from a side of the unit in such a way, the cleaning and disinfecting unit 100 in which a lot of elements are arranged on the disinfectant solution tank 32 may be reduced in size.

Facing the internal end opening of the bottle insertion hole 63, are the upper end sections of the laterally curved bottle attaching sections 43. In this case, the bottle receiving sections 43a of the bottle attaching sections 43 are located at a lower part in the bottle insertion hole 63. That is, when the bottles 50A and 50B are set in the bottle insertion hole 63 with their mouth sections 51a down as shown in FIG. 2. In this position, the mouth sections 51a (cap 52) can be-attached to the bottle receiving sections 43a. However, when the bottles 50A and 50B are set in the bottle insertion hole 63 with the mouth sections 51a up, the mouth sections 51a (cap 52) cannot be attached to the bottle receiving sections 43a. Accordingly, the bottle section 50 is prevented from being reversed.

A bottle detecting sensor 62 is arranged in the bottle insertion hole 63 to detect the bottles 50A and 50B being appropriately connected to the bottle attaching sections 43. The bottle detecting sensor 62 is actuated when it comes into contact with the bottle section 50 at the position, as shown in FIG. 5(c), at which the bottles 50A and 50B are appropriately connected to the bottle attaching sections 43. Moreover, when the bottles 50A and 50B are appropriately connected to the bottle attaching sections 43, the bottle section 50 completely disappears in the bottle insertion hole 63. Information on detection from the bottle detecting sensor 62 is transmitted to the control section 42.

Figure 6:
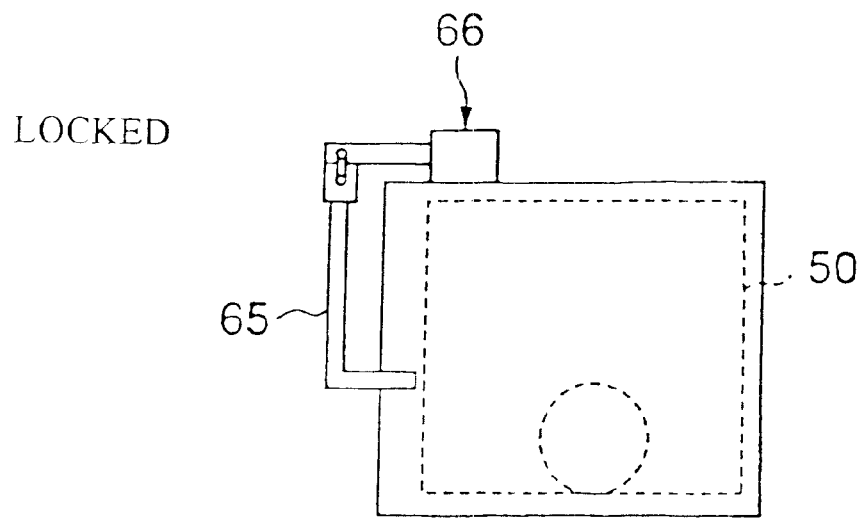
FIG. 6(a) shows the bottle is locked to the attachment section of the disinfectant solution section by the lock device.
FIG. 6(b) shows the lock device is released.

As shown in FIGS. 2 and 6, a lock device 66 is also arranged in the bottle insertion hole 63 to lock the bottle section 50 at the position, as shown in FIG. 5(c), at which the bottles 50A and 50B are appropriately connected to the bottle attaching sections 43. The lock device has a lock arm 65 for supporting the bottom face of the bottle section 50 to prevent the bottle section 50 from coming off from the bottle insertion section 63.

Next, an explanation will be given for how to inject a concentrated disinfectant solution into the disinfectant solution tank of the above-mentioned endoscope cleaning and disinfecting unit via the bottle section 50 for automatic dilution.

First, insert the bottle section 50 (holding a concentrated disinfectant solution in it) into the bottle insertion hole 63. The mouth sections 51a of the bottles 50A and 50B are closed off by the film sections 54 with the mouth sections down. As shown in FIG. 5(a), the caps of the bottles 50A and 50B face the bottle receiving sections 43a of the bottle attaching sections 43 on the side of the disinfectant solution tank 32. Next, when the bottle section 50 is further pushed into the bottle insertion hole 63, the cap bodies 52a of the caps 52 of the bottles 50A and 50B can be fitted to the ring-shaped space between the external tube a and the internal tube b, and the closed mouth sections 51a of the bottles 50A and 50B can be received by the bottle receiving sections 43a. In this case, the sealing section 52c is pressed by the inner face of the external tube a, and is elastically deformed to maintain the mouth sections 51a watertight to the outside(See FIG. 5(b)). When the bottle section 50 is further pushed into the bottle insertion hole 63, the film sections 54 can be ruptured by the protruding sections 43b, and the mouth sections 51a can be opened while the mouth sections 51a are received in watertight fashion as shown in FIG. 5(c). This allows the inside of the bottles 50A and 50B to communicate with the inside of the disinfectant solution tank 32 via the injection port 43c, and the solution in the bottles 50A and 50B can be completely injected into the disinfectant solution tank 32 because of the shape of the bottles 50A and 50B.

When the bottle section 50 is completely connected to the bottle attaching sections 43 in such a way, the bottle detecting sensor 62 comes contact with the bottle section 50, and is actuated. The information on detection is transmitted to the control section 42, and the control section 42 actuates the lock device 66 based on the information on detection. This allows the lock arm 65 to support the bottom face of the bottle section 50 (see FIG. 6(a)), and prevents the bottle section 50 from coming off from the bottle insertion hole 63.

When the first sensor 44 detects the predetermined quantity of the concentrated solution (the entire quantity of the solution held by the bottle section 50) being injected into the tank 32, the control section 42 opens the water feed valve 36, and switches the duct switching valve to connect the water duct 35 to the diluting solution supply duct 39. This allows cleaning water as a diluting solution to be injected into the disinfectant solution tank 32. Then, when the concentrated solution is diluted by the diluting solution, and the quantity of the disinfectant solution is detected by the second level sensor 45, the control section 42 judges that the concentration of the disinfectant solution has attained the predetermined level, and stops supplying the diluting solution to the disinfectant solution tank 32.

Figure 6B:
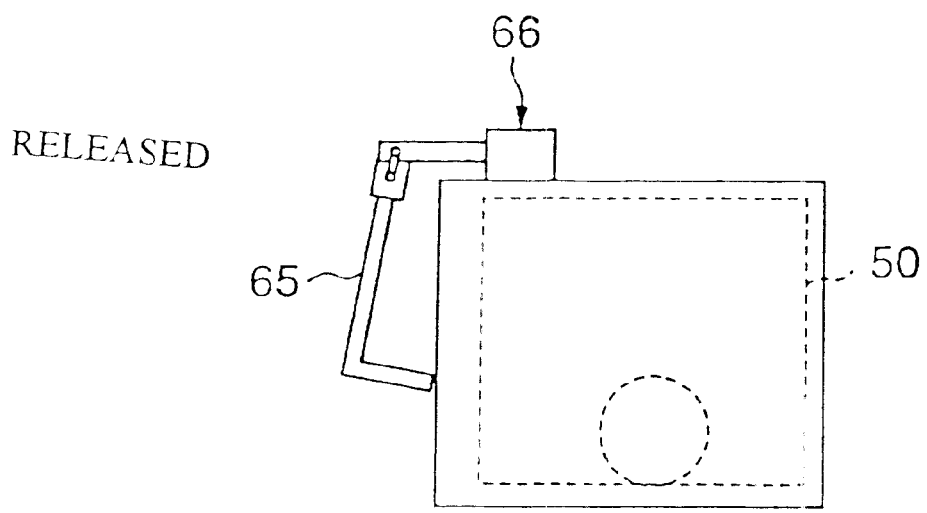

On the other hand, when the disinfectant solution in the disinfectant solution tank 32 is reduced to a predetermined quantity due to use of the disinfectant solution, the third level sensor 46 detects it. Then, the control section 42 encourages the user to discharge the disinfectant solution from the disinfectant solution tank 32. After the disinfectant solution has been discharged, and the first level sensor 44 has come to the off state, the control section 42 judges that the disinfectant solution has been discharged, and releases the lock device 66. (See FIG. 6(b)) This allows the user to take out the bottle section 50 and replace it with another. After a disinfectant solution has been automatically prepared through the above-mentioned processes, it becomes possible to clean and disinfect the endoscope 2.

As mentioned above, the bottle section 50 (bottles 50A and 50B) according to the present embodiment, which has a detachable section 60 and a sealing section 52c, can be directly connected to the bottle attaching section 32 (inlets) of the disinfectant solution tank 32 of the endoscope cleaning and disinfecting unit 100. Before the bottles 50A and 50B are attached to the bottle attaching sections of the disinfectant solution tank 32, the mouth sections of the bottles 50A and 50B are closed off by the film sections 54. When the bottles 50A and 50B are connected to the bottle attaching sections 43 of the disinfectant solution tank 32, the inside of the bottles 50A and 50B can communicate with the inside of the disinfectant solution tank 32 in a watertight manner relative to the outside, and the concentrated solution in the bottles 50A and 50B can flow into the disinfectant tank 32 via the bottle attaching sections 43, because the film sections 54 have been automatically ruptured by the protruding sections 43b when the bottles 50A and 50B have been attached to the bottle attaching sections 43 of the disinfectant solution tank 32. Therefore, when injecting a disinfectant solution into the disinfectant solution tank 32, no vapor of the disinfectant solution can leak out.

In the bottle section 50 (bottles 50A and 50B) according to the present embodiment, the sealing sections 52c are arranged on the top side of the bottle bodies 51 in a farther position from the mouth sections 51a than the film sections 54. Therefore, the bottles 50A and 50B can be connected to the bottle attaching sections 43 of the disinfectant solution tank 32 in a watertight and airtight manner. That is, the inside of the bottles 50A and 50B and the inside of the disinfectant solution tank 32 can communicate with each other after being cut off from the outside in a watertight and airtight manner. Therefore, the concentrated disinfectant solution in the bottles 50A and 50B can flow into the disinfectant solution tank 32 via the bottle attaching sections 43 without leaking out.

As for the bottle section 50 (bottles 50A and 50B) according to the present embodiment, its internal volume is set within a given range. That is, when the endoscope cleaning and disinfecting unit 100 requires a 15-liter disinfectant solution whose dilution rate is set at 10 times (nine-unit diluting solution to one-unit concentrated solution), the internal volume of the bottle section 50 is set at 1.05 to 2 liters. Therefore, a concentrated solution of an appropriate dilution rate can be supplied into the cleaning tank 1. (A concentrated solution can be supplied within a volume range predetermined by the unit.)

As for the bottle body 51 according to the present embodiment, the bottle 50A and the bottle 50B are integrally assembled without longitudinally deviating from each other by engaging the concave sections 55 on a sidewall with the convex sections 56 on another sidewall. Therefore, two kinds of solutions (in the present embodiment, the main agent and buffer) can be simultaneously and surely injected into the disinfectant solution tank 32.

As for the bottle section 50 (bottles 50A and 50B) according to the present embodiment, the mouth section 51a is eccentric to the center axis of the bottle body 51. Specifically, the mouth section 51a is located on the outer circumference of the bottle body 51 so that the inner face of a sidewall of the bottle body 51 may be on the same plane as the inner face of the mouth section 51a. Therefore, even when the bottles 50A and 50B lying on their side are engaged with the bottle insertion holes 63, solutions held in the bottles 50A and 50B may be completely discharged due to their own weight.

When the mouth section 51a is eccentric to the center axis of the bottle body 51, the bottle section 50 can be prevented from being reversedly inserted if the bottle receiving section 43a of the bottle attaching section 43 is leaned in the bottle insertion hole 63.

Although in the present embodiment, the bottle section 50 (bottles 50A and 50B) attaches to the disinfectant solution tank of an endoscope cleaning and disinfecting unit, it may used with the disinfectant solution tank of a unit for cleaning and disinfecting some other instrument other than the endoscope. In addition, although in the present embodiment, the film section 54 is arranged on the cap 52, it may be arranged on the side of the bottle body 51. Moreover, although in the present embodiment, the bottle section 50 (bottles 50A and 50B) is used as a bottle for supplying a concentrated disinfectant solution, it may be used as a bottle for supplying an already prepared disinfectant solution. In this case, it can even be used with a cleaning and disinfecting unit having no automatic dilution function.

FIG. 7 shows a second embodiment according to the present invention. In the present embodiment, the bottle detecting sensor 62 is not a contact-sensor like in the first embodiment, but a photo-sensor. In addition, as shown in FIG. 7, the bottles 50A and 50B have a convex section 70 on their bottle body 51 that can be detected by the photo-sensor (i.e. can block light passing from the light emitting section to the light receiving section). Moreover, on a sidewall of each bottle body 51, is formed a concave section 72 with which the lock arm 65 of the lock device 66 can engage. The entire configuration is the same as that of the first embodiment except as mentioned above.

When the convex sections 70 arranged on the bottles 50A and 50B are detected by a photo-sensor, only a bottle holding a disinfectant solution the concentration of which is controlled as predetermined can be attached.

FIG. 8 shows a third embodiment according to the present invention. In the present embodiment, the bottles 50A and 50B have no resin film section 54 like the first or second embodiment, but an aluminum-foil film welded on their bottle body 51. The entire configuration is the same as that of the first embodiment except as mentioned above.

Figures 9A, 9B:
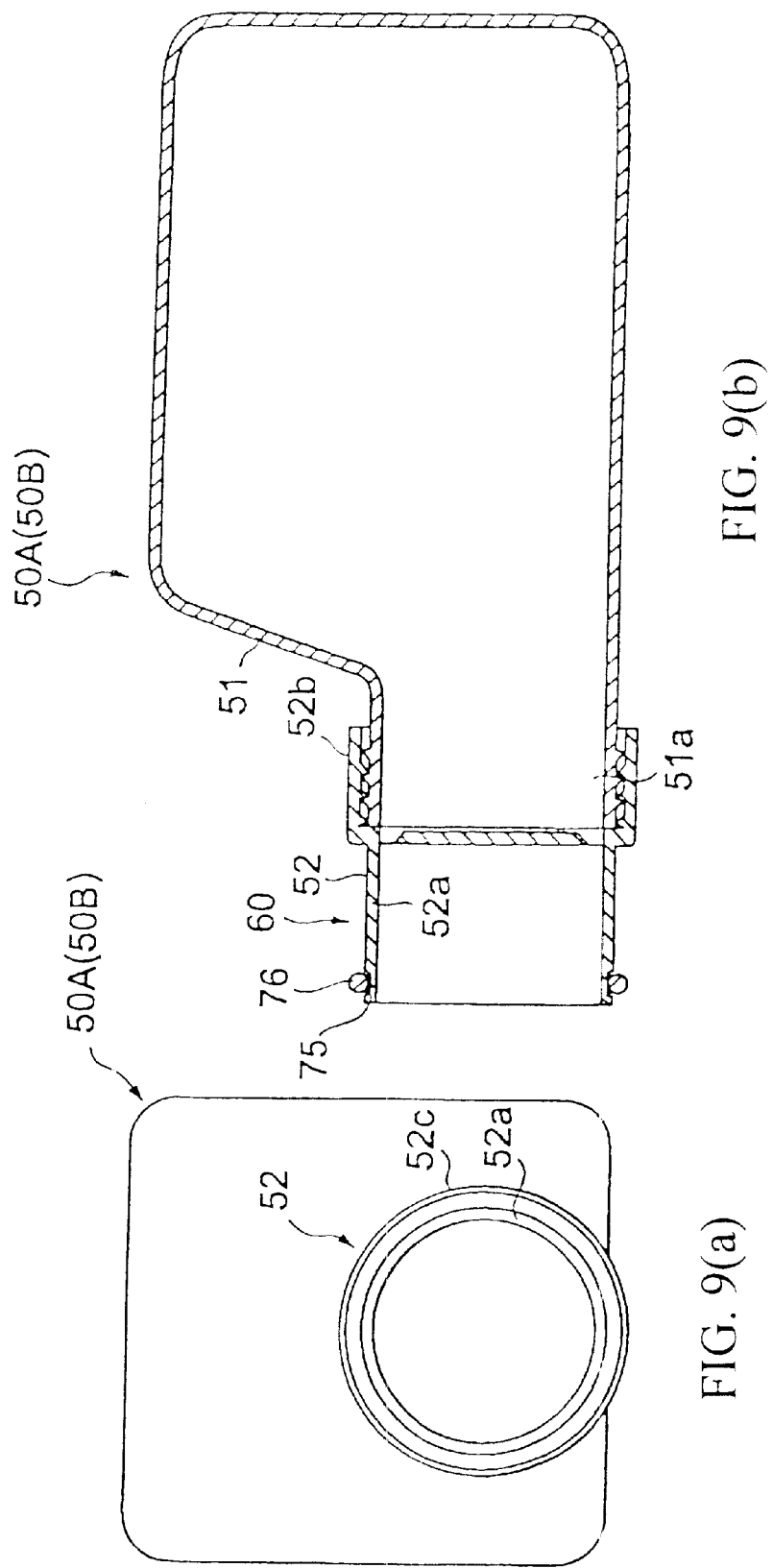
FIG. 9(a) is a front view of the mouth section of the bottle according to the forth embodiment of the invention.
FIG. 9(b) is a cross-sectional view of the bottle shown in FIG. 9(a).

FIG. 9 shows a forth embodiment according to the present invention. In the present embodiment, the bottles 50A and 50B have no sealing section 52c comprising an elastic-material member formed at the distal end of the cap body 52a. Instead, a ring-shaped groove 75 is arranged on the circumferential face of the distal end section of the cap body 52a, and provided with an O-ring 76. The entire configuration is the same as that of the first embodiment except as mentioned above.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A disinfectant solution bottle comprising:
   a bottle body for holding a disinfectant solution or concentrated disinfectant solution;
   a detachable section disposed at a mouth section of said bottle body;
   means for closing off said mouth section of said bottle body, said means for closing off formed such that said means for closing off may be ruptured to open said mouth section; and
   a sealing section disposed on said detachable section at a tip thereof, for keeping said mouth section of said bottle body watertight and airtight to the outside when said bottle is connected to an inlet of a disinfectant solution tank, wherein said detachable section is tubular and adapted to slidably engage a tubular inlet of a disinfectant solution tank.

2. A disinfectant solution bottle according to claim 1, wherein said bottle body has a threaded neck terminating in said mouth section and said tubular detachable section has an end opposite to said tip with threads, and is screwed onto said neck.

3. A disinfectant solution bottle according to claim 1, wherein said sealing section is disposed at a further position from said mouth section than said means for closing off on the tip of said bottle body.

4. A disinfectant solution bottle according to claim 1, wherein the internal volume of the bottle body is set at 1.05 to 2 liters for use with an endoscope cleaning and disinfecting unit that requires a 15-liter disinfectant solution, and whose dilution rate is set at 10 times.

5. A disinfectant solution bottle according to claim 1, wherein the center axis of said mouth section is eccentric to the center axis of the bottle body.

6. A disinfectant solution bottle according to claim 5, wherein an inner face of a sidewall of the bottle body may be in the same plane as the inner face of the mouth section.

7. A disinfectant solution bottle according to claim 1, wherein the bottle body has a convex section that can be detected by a sensor to detect the bottle being appropriately connected to an inlet of a disinfectant solution tank.

8. A disinfectant solution bottle according to claim 1, wherein said bottle body has a bottle holding a concentrated A solution, and another bottle holding a concentrated B solution, both of which are integrally assembled without longitudinally deviating from each other by engaging concave sections arranged on the bottle body of a bottle with convex sections arranged on the bottle body of another bottle.

9. A disinfectant solution bottle according to claim 1, wherein said detachable section is attached to said bottle body in a detachable manner.

10. A disinfectant solution bottle according to claim 1, wherein said means for closing off comprises a film to seal said mouth section.

11. A disinfectant solution bottle according to claim 3, wherein said means for closing off comprises a film to seal said mouth section.

12. An endoscope cleaning and disinfecting unit, comprising:
    a cleaning tank;
    a disinfectant solution tank for holding a disinfectant solution to be supplied to said cleaning tank and having an inlet;
    a disinfectant solution bottle attached to the inlet of the disinfectant solution tank in a detachable manner comprising:
    a bottle body for holding a disinfectant solution or concentrated disinfectant solution;
    a detachable section disposed at a mouth section of said bottle body and detachably attached to the inlet of a disinfectant solution tank;
    means for closing off said mouth section of said bottle body, said means for closing off formed such that said means for closing off may be ruptured to open said mouth section; and
    a sealing section disposed on said detachable section at a tip thereof, attached to said inlet of said disinfecting solution tank, for keeping said mouth section of said bottle body watertight and airtight to the outside.

13. An endoscope cleaning and disinfecting unit according to claim 12, wherein said inlet comprises a tubular opening and said detachable section is also tubular, at least in the area of said tip, said area of said tip inserted in said tubular opening with said sealing section engaging the inside of said tubular opening in a watertight and airtight manner.

14. An endoscope cleaning and disinfecting unit according to claim 12, wherein said sealing section is disposed at a further position from said mouth section than said means for closing off on the tip of said bottle body.

15. An endoscope cleaning and disinfecting unit according to claim 12, wherein the internal volume of the bottle body is set at 1.05 to 2 liters when the cleaning and disinfecting unit requires a 15-liter disinfectant solution whose dilution rate is set at 10 times.

16. An endoscope cleaning and disinfecting unit according to claim 12, wherein the center axis of said mouth section is eccentric to the center axis of the bottle body.

17. An endoscope cleaning and disinfecting unit according to claim 16, wherein an inner face of a sidewall of the bottle body may be in the same plane as the inner face of the mouth section.

18. An endoscope cleaning and disinfecting unit according to claim 12, wherein the bottle body has a convex section that can be detected by a sensor to detect the bottle being appropriately connected to the inlet of the disinfectant solution tank.

19. An endoscope cleaning and disinfecting unit according to claim 12, wherein said bottle body has a bottle holding a concentrated A solution, and another bottle holding a concentrated B solution, both of which are integrally assembled without longitudinally deviating from each other by engaging concave sections arranged on the bottle body of a bottle with convex sections arranged on the bottle body of another bottle.

20. An endoscope cleaning and disinfecting unit according to claim 12, wherein said disinfectant tank has opening means for rupturing said means for closing off.

21. An endoscope cleaning and disinfecting unit according to claim 12, wherein said detachable section is to said bottle body in a detachable manner.

22. An endoscope cleaning and disinfecting unit according to claim 12, wherein said means for closing off comprises a film to seal said mouth section.

23. An endoscope cleaning and disinfecting unit according to claim 14, wherein said means for closing off comprises a film to seal said mouth section.

24. An endoscope cleaning and disinfecting unit according to claim 20, wherein said means for closing off comprises a film to seal said mouth section.

* * * * *

UNITED STATES PATENT AND TRADEMARK OFFICE
CERTIFICATE OF CORRECTION

PATENT NO.    : 6,656,438 B1
DATED         : December 2, 2003
INVENTOR(S)   : Toshiharu Kinoshita et al.

It is certified that error appears in the above-identified patent and that said Letters Patent is hereby corrected as shown below:

Column 12,
Line 2, after "section is" insert -- attached --.

Signed and Sealed this

Twelfth Day of October, 2004

JON W. DUDAS
*Director of the United States Patent and Trademark Office*